United States Patent [19]

Bahrmann et al.

[11] Patent Number: 5,661,204
[45] Date of Patent: *Aug. 26, 1997

[54] MIXTURES OF ISOMERIC DECYL ALCOHOLS, PHTHALATES OBTAINABLE THEREFROM, AND THEIR USE AS PLASTICIZERS

[75] Inventors: Helmut Bahrmann, Hamminkeln; Wolfgang Greb, Dinslaken; Peter Heymanns, Essen; Peter Lappe; Thomas Müller, both of Dinslaken; Jürgen Szameitat, Wesel; Ernst Wiebus, Oberhausen, all of Germany

[73] Assignee: Hoechst Aktiengesellschaft, Germany

[*] Notice: The term of this patent shall not extend beyond the expiration date of Pat. No. 5,369,162.

[21] Appl. No.: 484,587

[22] Filed: Jun. 7, 1995

Related U.S. Application Data

[62] Division of Ser. No. 83,631, Jun. 28, 1993, abandoned.

[30] Foreign Application Priority Data

Jun. 30, 1992 [DE] Germany .................. 42 21 472.6

[51] Int. Cl.$^6$ ................ C08K 5/09; C07C 69/76
[52] U.S. Cl. .................. 524/296; 524/297; 568/840; 568/882; 560/76
[58] Field of Search ................ 524/296, 297; 568/840, 882; 560/76

[56] References Cited

U.S. PATENT DOCUMENTS

| | | | |
|---|---|---|---|
| 4,922,028 | 5/1990 | Oswald et al. | 568/448 |
| 5,268,514 | 12/1993 | Bahrmann et al. | 568/882 |
| 5,369,162 | 11/1994 | Bahrmann et al. | 524/296 |
| 5,462,986 | 10/1995 | Bahrmann et al. | 524/296 |

FOREIGN PATENT DOCUMENTS 0366089  5/1990  Japan .

Primary Examiner—Joseph L. Schofer
Assistant Examiner—John J. Guarriello
Attorney, Agent, or Firm—Bierman, Muserlian & Lucas

[57] ABSTRACT

Mixtures of isomeric decyl alcohols obtained by oligomerization of propylene in the presence of deactivated zeolites as catalysts, followed by separation of the nine carbon olefins from the oligomer mixture, then hydroformylation of the 9 carbon olefins to 10 carbon aldehydes, and hydrogenation of the aldehydes to the corresponding alcohols. The mixtures, when esterified with phthalic acid, or anhydride, provide a mixture of isomeric di-decyl phthalates that can be used as plasticizers.

2 Claims, No Drawings

MIXTURES OF ISOMERIC DECYL ALCOHOLS, PHTHALATES OBTAINABLE THEREFROM, AND THEIR USE AS PLASTICIZERS

This is a Division of Ser. No. 083,631 filed Jun. 28, 1993 abandoned.

This application claims the priority of German application P 42 21 472.6, filed Jun. 30, 1992.

The present invention relates to mixtures of isomeric decyl alcohols, to a process for their preparation, to the phthalates obtained from these alcohols, and to their use as plasticizers.

BACKGROUND OF THE INVENTION

Esters of phthalic acid are used in large amounts as plasticizers, in particular for polyvinyl chloride. The alcohol components are predominantly primary alcohols having 8 to 10 carbon atoms, of which 2-ethylhexanol is currently the most important. Phthalates formed from shorter-chain alcohols provide plasticizers Having a good gelling strength. However, their greater volatility is a disadvantage compared to longer-chained compounds. Longer- chain esters, on the other hand, gel more slowly and have less resistance to low-temperatures.

The properties of phthalate plasticizers are influenced by the size of the alcohol molecule and also by the branching of the carbon chain. For example, alcohols with few branches produce ester plasticizers that are particularly valued despite their high low-temperature flexibility. Predominantly linear alcohols having 9 to 10 carbon atoms in the molecule are therefore becoming increasingly important as the alcohol components. A precondition for their use is that they are available in large amounts and are relatively inexpensive.

Throughout the specification and claims, all percents are by weight unless otherwise indicated. According to German Patent 2 855 421, the plasticizers used are phthalates of alcohols having 9 carbon atoms, which are obtained by the oxo reaction of 8 carbon olefins, hydrogenation of the reaction product, and esterification of the resulting 9 carbon alcohols with phthalic anhydride. From 3% to 20% of the starting olefins should have an isobutane skeleton in each molecular chain, less than 3% of the olefins contain quaternary carbon, and more than 90% of the total amount of the olefins are present as n-octenes, monomethylheptenes, and dimethylhexenes. Furthermore, the weight ratio of the total amount of n-octenes and monomethylheptenes to the dimethylhexenes should be more than 0.8.

Phthalates based on 10 carbon alcohols are the subject of European Patent Application 366,089. These alcohols are used as a mixture obtained by hydroformylation of a butene fraction, aldol condensation of the resultant aldehyde mixture, and subsequent hydrogenation.

Another route for obtaining di-decyl phthalate mixtures is described in European Patent Application 424,767. The esters are prepared by a multistage process involving dimerization of butene mixtures, hydroformylation and hydrogenation of the resulting octene mixture to form a nonanol mixture, dehydration of the nonanol mixture to form a nonene mixture, and hydroformylation and hydrogenation of the nonene mixture to a mixture of decanols.

The known processes still do not satisfy, as regards economic and technical aspects, all requirements that are placed on a process employed on a large scale. The starting materials are not available in sufficient amounts, they are too expensive, and/or the conversion of the starting materials into the alcohols involves processes that are too complicated. The object of the invention is, therefore, to develop a process that starts from raw materials that are available at a reasonable price and which can be converted into the desired alcohols in a technically simple manner.

SUMMARY OF THE INVENTION

A portion of the invention consists of mixtures of isomeric decyl alcohols, and a method of their preparation. These decyl alcohols are obtained by oligomerization of propylene in the presence of deactivated zeolites as catalysts, followed by separation of the 9 carbon olefins from the oligomer mixture formed, then hydroformylation of the mixture to 10 carbon aldehydes, and hydrogenation of the aldehydes to the corresponding alcohols.

DETAILED DESCRIPTION OF THE INVENTION

The carbon olefins used as starting materials for the preparation of the mixtures of isomeric decyl alcohols of the invention are the product of the oligomerization of propylene in the presence of deactivated zeolites. The oligomerization of low molecular weight olefins, such as propylene, n-butene, i-butene, n-pentene, under the action of special zeolites is a known reaction, and is described, for example, in U.S. Pat. No. 4,982,031. The catalytically active zeolites are preferably of the ZSM-5 type, the surfaces of which have been deactivated with a sterically hindered base, e.g. a trialkylated pyridine. When propylene is used as the olefin, for example, an oligomer mixture comprising essentially monoolefins having 6, 9, 12, 15, 18, and 21 carbon atoms are produced. It is particularly significant that these olefins are largely unbranched. Based on the compounds of different molecular size in the oligomer mixture, there are only about one to two methyl branches for every 15 carbon atoms arranged in an unbranched chain. Due to the low degree of branching, the 9 carbon olefins obtained as described hereinbefore differ recognizably from the propylene oligomer termed tripropylene, which is prepared from propylene in the presence of acid catalysts, in particular phosphoric acid or sulfuric acid, and which comprises a mixture of highly branched nonenes.

To isolate the 9 carbon olefins which are intended to be processed further, the oligomerization product is separated in a conventional way by distillation into individual fractions. The nonene fraction that is obtained can be hydroformylated without additional purification stages.

The hydroformylation of the 9 carbon olefin mixture is carried out by the prior art processes in the usual manner, using cobalt as well as rhodium as the catalyst. The reaction can be carried out in the homogeneous liquid phase, with catalysts that are soluble in organic media, or can be carried out in heterogeneous reaction systems, with catalysts that are dissolved in water. The latter procedure has been found to be particularly suitable in conjunction with rhodium catalysts.

In the case of hydroformylation in homogeneous reaction systems, the conventional process with cobalt catalysts is used. Temperature of 90° C. to 150° C., pressures of 10 to 30 MPa, and catalyst concentrations of 0.1% to 1.5% of cobalt, based on the olefin employed, are the standard reaction conditions. Instead of cobalt, the hydroformylation catalyst may also be rhodium, which is substantially more active than cobalt and is therefore used in a lower concentration. The reaction is normally carried out at 80° to 200°

C. and pressures of 10 to 60 MPa. 0.1 to 50 mg, preferably 2 to 10 mg, of rhodium is used per kg of olefin. An effective catalyst compound in both cases is hydridocarbonyl HMe $(CO)_4$, wherein Me is cobalt or rhodium.

Instead of catalyzing the conversion of the olefin mixture to aldehydes using simple carbonyl compounds, modified carbonyl compounds of cobalt or rhodium may also be successfully used. Modified carbonyl compounds are compounds of the aforementioned metals which also contain, in the molecule, further complex ligands other than carbon monoxide. This variant of the hydroformylation reaction also belongs, when cobalt catalysts and rhodium catalysts are used, to the prior art. Preferred complex ligands are organic compounds of trivalent phosphorus. Examples of such compounds are triarylphosphines, such as triphenylphosphine; trialkylphosphines, such as tributylphosphine; tri(alkyl/aryl)phosphines, such as diethylphenylphosphine; triaryl phosphites, such as triphenyl phosphite; trialkyl phosphites, such as triethyl phosphite; tri(alkyl/aryl) phosphites; and phospholes. Also suitable are bidentate ligands, i.e. diphosphines or diphosphites, which contain two phosphorus(III) atoms capable of participating in complex formation; among these compounds those which form chelates with the metal atoms are preferred. Particularly suitable as ligands are sterically hindered phosphites capable of participating in the chelate formation, which form, with the inclusion of the central metal atom, rings containing nine atoms. Such phosphites are described, for example, in EP 353,770 A2 and in EP 435,071 A2.

The ligands are normally used in excess, i.e. in an amount that is greater than that required for the complex formation. The ratio of metal atoms to ligand molecules (in moles) of 1:5 to 1:100 has been found suitable in practice; as is known, this ratio depends on, inter alia, the nature of the ligand. Modified cobalt or rhodium catalysts permit the use of lower reaction pressures than unmodified catalysts, pressures of 0.1 to 10 MPa, especially 0.5 to 6 MPa, being customary. The reaction temperatures, when modified cobalt catalysts are used, are 140° to 180° C.; they are higher than in the case of the corresponding rhodium catalysts, which require temperatures of only 90° C. to 130° C. The synthesis gas used for the hydroformylation preferably contains about equal volumes of hydrogen and carbon monoxide, though variations from this composition in either direction are not harmful.

In the heterogeneous phase, the hydroformylation of the 9 carbon olefins is carried out in a two-phase system, an embodiment of the oxo synthesis, which is described, e.g. in German Patent 26 27 354. Such a process is characterized by two liquid phases; namely, an organic phase, which contains the starting olefin and the reaction product, and an aqueous phase, in which the catalyst is dissolved. Water soluble rhodium complex compounds with water soluble phosphines as ligands have been found to be suitable as catalysts. Water-soluble phosphines include triarylphosphines, trialkylphosphines, alkyldiphosphines, aryldiphosphines, and alkylaryldiphosphines, whose organic radicals have been substituted by sulfonyl groups or carboxyl groups. The reaction is carried out at 60° to 150° C., preferably 90° to 120°, and under pressures of 0.4 to 30 MPa, in particular 1 to 10 MPa. The rhodium concentration is 20 to 2000 ppm by weight, preferably 50 to 500 ppm by weight, based on the aqueous catalyst solution, and 4 to 100 mol of water-soluble phosphine are used per mol of rhodium. The volume ratio of aqueous phase to organic phase is from 0.1 to 10: 1.

The olefin conversion is significantly increased if a phase transfer reagent (solubilizer) is added to the aqueous catalyst solution. Particularly suitable are cationic solubilizers of the formula $[A-N(R^1R^2R^3)]^+E^-$, in which A is a straight or branched chain alkyl radical having 6 to 25 carbon atoms; $R^1$, $R^2$, and $R^3$ are individually straight or branched chain alkyl radicals having 1 to 4 carbon atoms; and $E^-$ is any anion, in particular it is sulfate, tetrafluoroborate, acetate, methosulfate, benzenesulfonate, alkylbenzenesulfonate, toluenesulfonate, lactate, for citrate.

The hydroformylation of the 9 carbon olefins according to the invention with cobalt or rhodium as catalyst, which is carried out either in the one- or two-phase reaction system, produces a mixture of isomeric decanals in high yield. This mixture contains 80% or more straight-chain 10 carbon aldehydes, and only minor amounts of methyl-branched and dimethyl-branched aldehydes. The composition of the aldehyde mixture can be influenced by varying the reaction conditions and/or the catalyst, in particular by the choice of ligand when using modified carbonyls.

After completion of the hydroformylation, the aldehyde mixture is separated from the catalyst, from the unconverted reactants, and from the other reaction products. Distillation is the normal separation process when carrying out the reaction in the homogeneous phase. If the hydroformylation was carried out in the two-phase system, the product and catalyst can be recovered merely by phase separation. This process is substantially simpler in its technical execution and, on account of the absence of high temperatures, is also considerably more gentle than the distillative isolation of the aldehyde mixture. The hydroformylation of the 9 carbon olefin mixture may be carried out batchwise or continuously, irrespective of the process employed.

The isomeric decanals separated from the remaining constituents of the reaction mixture are then hydrogenated to the desired decyl alcohol mixture. The addition of hydrogen is effected in known manner in the presence of catalysts. Suitable hydrogenation catalysts are, for example, based on nickel, chromium, or copper. The hydrogenation temperature is generally from 100° to 180° C., and pressure is 1 to 10 MPa; the decyl alcohol mixture is then purified by distillation. The mixture is highly suitable as the alcohol component in phthalates that are to be used as plasticizers. The preparation of the phthalates is known [cf. Ullmann, Encyclopädie der Technischen Chemie (1979), Vol 18, p. 536 ff]. Phthalic anhydride is expediently reacted with the decyl alcohol mixture in one stage in a molar ratio of 1:2. The reaction rate can be increased by using catalysts and/or raising the reaction temperature. In order to displace the equilibrium in the direction of ester formation, the water formed must be removed from the reaction mixture. The phthalates obtained from the decyl alcohol mixture according to the invention are plasticizers characterized by outstanding low-temperature properties.

The invention is illustrated in more detail in the following example, but is not restricted to this specific embodiment.

EXAMPLE.

1. Starting olefin mixture

An oligomeric propylene is used that has been obtained by reacting propylene on a deactivated zeolite as the catalyst. It comprises about 87.3% tripropylene and 12.7% tetrapropylene. A high proportion of the olefins is linear, a very small amount being slightly branched.

2. Hydroformylation 500 g of the olefin mixture, 10 g of $CoCO_3$, and 15 g of water are reacted with water gas ($H_2:CO=1:1$) in a 1 liter autoclave at 170° C. and 27 MPa for 4 hours. The autoclave contents are decompressed and cooled, and 52 g of water is added. The autoclave is re-closed and heated to 190° C. for 2 hours with stirring. The contents are cooled and the organic and aqueous phases are separated from one another. 549 g of crude aldehyde is obtained.

3. Hydrogenation

The crude aldehyde is treated with hydrogen in a 2.8 liter autoclave at 150° C. and under a pressure of 10 MPa in the presence of a nickel catalyst (10% by volume, based on the starting materials). The contents are then cooled, the pressure is released, and the contents are hydrogenated again under the same reaction conditions with the addition of a further 5% by volume of a nickel catalyst. The reactor is cooled, the pressure is released, and the crude alcohol product is separated from the nickel catalyst by filtration.

4. Distillation 825.5 g of the crude alcohol is then distilled in a 1 meter column containing glass rings 5 mm in diameter. A first running is removed at an overhead temperature of 100° C. and 13.3 kPa pressure, and an intermediate cut is removed at 135° C. and 6.7 kPa pressure. The main fraction is obtained at an overhead temperature of 147° C. and 6.7 kPa. Gas chromatography analysis shows an alcohol content of 95.7%; the yield of pure 10 carbon alcohol, based on the feedstock olefin, is 72% of theoretical.

5. Esterification 380.4 g (2.3 mol) of the pure 10 carbon alcohol and 148.1 g (1 mol) of phthalic anhydride are reacted at 135° C. in the presence of 0.59 g of concentrated sulfuric acid, the water formed in the reaction being removed. The reaction is complete after 6 hours, and the reaction product is neutralized with 5% sodium hydroxide solution. Steam distillation is then carried out at 135° C. and 15 kPa. The distillate is washed with water and then dried for 5 hours in a stream of nitrogen at 135° C. and 2 to 3 kPa. After filtration, a clear liquid is obtained having the following characteristic data:

| | |
|---|---|
| Ester content | 99.41% |
| Alcohol content | 0.22% |
| Pt/Co color index | 5–10 |
| Density (g/ml; 20° C.) | 0.9655 |
| Viscosity (mPa · s; 20° C.) | 108 |
| Acid number (mg KOH/g) | 0.06 |

The viscosity of the ester is considerably lower than the viscosity of currently available products based on conventional propylene polymers, which is 120 to 130 mPa.s/20° C. The ester is thus notable for its outstanding processing properties.

We claim:

1. The method of plasticizing a resin comprising incorporating therein a plasticizingly effective amount of a didecyl phthalate of a mixture of decyl alcohols which is the product of oligomerization of propylene, catalyzed by deactivated zeolite, to form an oligomer mixture comprising 9 carbon olefins, separation of said 9 carbon olefins from said oligomer mixture, hydroformylation of said 9 carbon olefins to 10 carbon aldehydes, and hydrogenation of said aldehydes to said decyl alcohols, said mixture being at least 80% linear and containing minor amounts of methyl-branched and dimethyl-branched decyl alcohols.

2. The method of claim 1 wherein said resin comprises polyvinyl chloride.

* * * * *